US011766960B1

(12) United States Patent
Ferguson et al.

(10) Patent No.: US 11,766,960 B1
(45) Date of Patent: Sep. 26, 2023

(54) EMAN'S TRUCKER PILLOW (71) Applicants: Rhonda King Ferguson, Covington, GA (US); Emanuale Isaiah King, Covington, GA (US)

(72) Inventors: Rhonda King Ferguson, Covington, GA (US); Emanuale Isaiah King, Covington, GA (US)

( * ) Notice: Subject to any disclaimer, the term of this patent is extended or adjusted under 35 U.S.C. 154(b) by 17 days.

(21) Appl. No.: 17/591,771

(22) Filed: Feb. 3, 2022

Related U.S. Application Data

(60) Provisional application No. 63/290,370, filed on Dec. 16, 2021.

(51) Int. Cl.
*B60N 2/75* (2018.01)
*A61F 5/37* (2006.01)
*A47C 20/02* (2006.01)

(52) U.S. Cl.
CPC ............ *B60N 2/787* (2018.02); *A47C 20/023* (2013.01); *A61F 5/3761* (2013.01)

(58) Field of Classification Search
CPC ...... A61F 5/373; A61F 5/3723; A61F 5/3761; A47C 20/023; A47C 7/546; B60N 2/787; A47D 13/083; A61M 5/52
See application file for complete search history.

(56) References Cited

U.S. PATENT DOCUMENTS

| | | | | |
|---|---|---|---|---|
| 4,941,480 A | * | 7/1990 | McLean | A61F 5/05841 128/878 |
| 5,332,288 A | * | 7/1994 | Coates | B60N 2/787 296/153 |
| 2013/0000042 A1 | * | 1/2013 | Ferrell | A47G 9/10 5/636 |
| 2013/0341979 A1 | * | 12/2013 | Girard | A47C 7/021 297/227 |
| 2016/0297378 A1 | * | 10/2016 | Humphrey | B60R 13/0262 |

* cited by examiner

*Primary Examiner* — Daniel J Colilla (57) ABSTRACT

The invention provides a portable wearable trucker pillow. The pillow structure is poly fiber or foam padding. The trucker pillow functions to protect the arms, face, and upper body wearing pillows on each arm. The truck driver does have auto collision that causes flying glass and debris that causes facial and upper body injuries. The trucker pillows give the drivers some added protection and support from a hard uncomfortable surface while driving. The straps or Velcro mid-section and hook loop are used as a carry-on aide. The pouch has underneath elastic bands or and Velcro are structures that assist the drivers arm snug to a fitted attached to a pillow. These pillows provide a barrier, protection, and support to the arms, while driving cars and trucks. The pillow also is an arm free device giving over the road truck drivers safety for DOT compliance a nonstationary arms free pillow. The pillow will be also used in sports activities as a protective barrier for face and upper body.

1 Claim, 10 Drawing Sheets

EMAN'S TRUCKER PILLOW

CROSS-REFERENCE TO RELATED APPLICATIONS

This application claims the benefit of U.S. Provisional application No. 63/290,370 filed Dec. 16, 2021, the entire contents of which are hereby incorporated by reference.

BACKGROUND OF THE INVENTION

Every day commercial truck drivers are in various accidents due to long hours of over the road driving. According to the National Center for Health Statistics, accidents are the third leading cause of death in the United States. Accidents are the main cause of death for people under the age of forty-Jive. The National Highway Traffic Safety Administration reported the nation lost 38,680 in motor vehicle traffic crashes in 2020. The death number is in the thousand's yearly accidents. The following statistics were published in March 2013 by the department of transportation and the federal Motor Carrier Safety Administration. These totals are in the 2012 values of the US dollar and account for all commercial vehicle crashes including fatal crashes, injury crashes, and property damage only crashes. 2009: $88 Billion, 2010: $93 Billion, 2011: $93.4 Billion. The Federal Motor Carrier Safety Administration breaks down average truck accidents that cost basic health and property damage $334,892. When a semi-truck is pulling multiple trailers 1.2 million per incident. When a semi-truck accident results in a fatality $7.2 million. Commercial drivers are over the road six to seven days a week, they work tirelessly twelve to fourteen hours per day according to DOT laws. However, most owner operator drivers work longer than these hours per day which cause fatigue and anxiety especially in their shoulders and arms. Ninety percent of drivers have health problems but can barely take time off for medical checkups. According to the Federal Motor Carrier Safety Administration one major problem with commercial drivers is their physical health. One widespread problem most commercial drivers have experienced is back and shoulder pain from poor circulation and lack of movement. What's needed is a simple tool product: a carrier on a portable and wearable driver's pillow to protect, support a stiff arm from going numb while driving long exhausting travel routes.

BRIEF SUMMARY OF THE INVENTION

This invention solves the problems of painful shoulders that need some comfort from the hard surfaces in a commercial truck and add support to an arm rest stationary in the truck. The portable wearing arm pillow will promote comfort and circulation while driving long hours. The pillow comprises of soft stretchable fleece fabrics. The drivers wearable pillow places their arms into a elastic bands covered by a pouch attached to a structure pillow allowing an arm free movement while driving long exhausted travel. The pouch is reversible; it can be worn on the drivers' arms or reverse; the opening pouch is placed over a stationary vehicle's object already located in the vehicle or and used by a passenger's arms. The carrying straps or Velcro straps are used to carry the pillow. The trucker's pillow functions also as a protective barrier; the arm pillow made of poly fiber and or foam padding will be used to protect the drivers and passenger face and upper body. Auto collisions will have flying glass and debris which will harm the drivers and passengers facial and upper body.

DETAILED DESCRIPTION OF THE INVENTION

Figure 1:
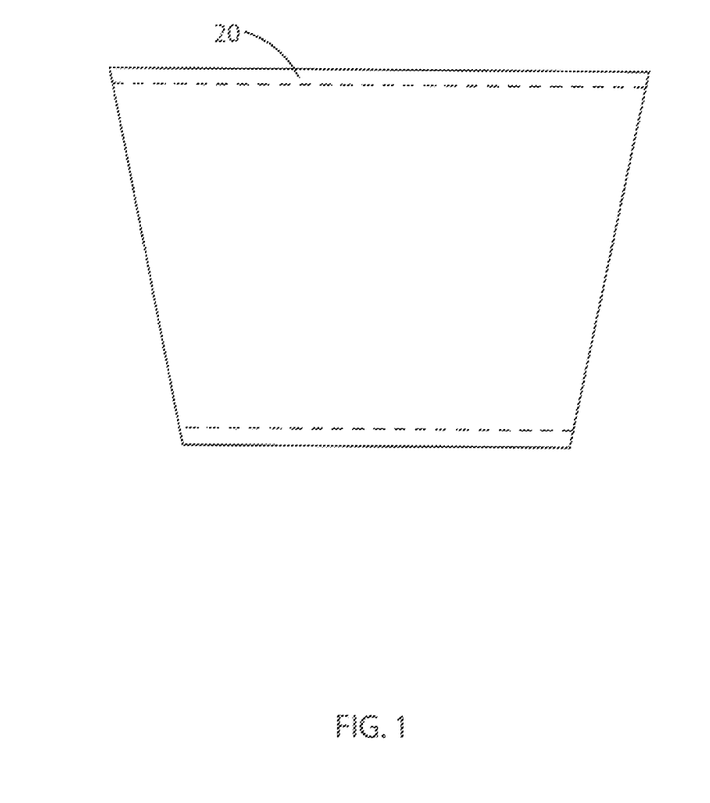
FIG. 1 depicts illustrates a pouch cover.
Figure 2:
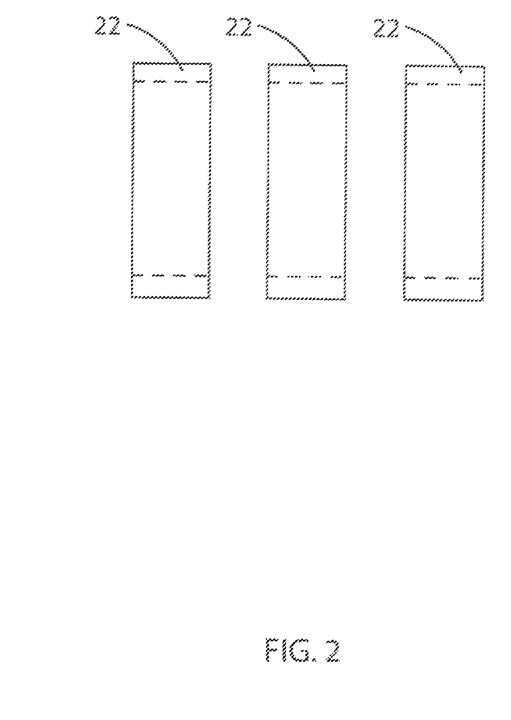
FIG. 2 depicts illustrate elastic bands.

In the following detailed description, the driver's portable wearable pillows will be described by the embodiment's figures. It should be noted that the trucker pillows are constructed to support the shoulders, elbow, wrist, and hand while driving long exhausting trips. The pillows are designed to assist the commercial truck drivers in relaxing their arms. The driver is under mental and physical stress their arm pain while driving long over the road exhausting trips will leave a drivers stiff and sore shoulders and elbows. FIGS. 1 and 2 shows a mixture of soft and stretchable fabric that attaches to a pillow in FIG. 1 items (20) as shown a pouch that fits snugged around a drivers arm stretchable fabric. Shown in FIG. 2 item (22) elastic bands attached to a pouch hugs the drivers arm fitted snugged taking pressure off the tired arm provide circulation to an arm fitting into a pouch over a pillow portable to carry and wearable any size arm inside and vehicle and outside for any sports activity.

Figure 3:
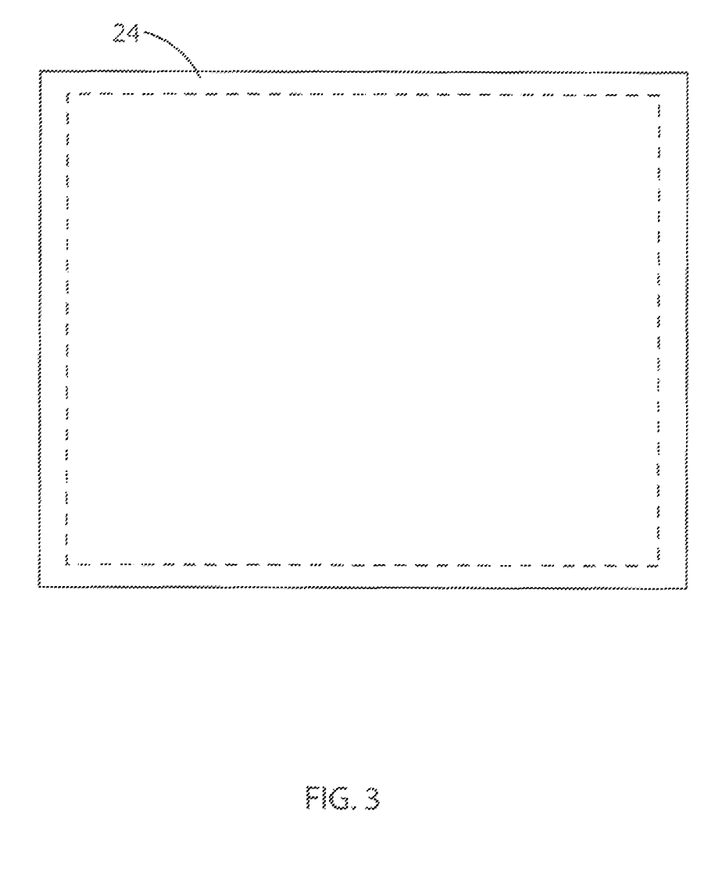
FIG. 3 illustrate a block diagram of a pillow.
Figure 4:
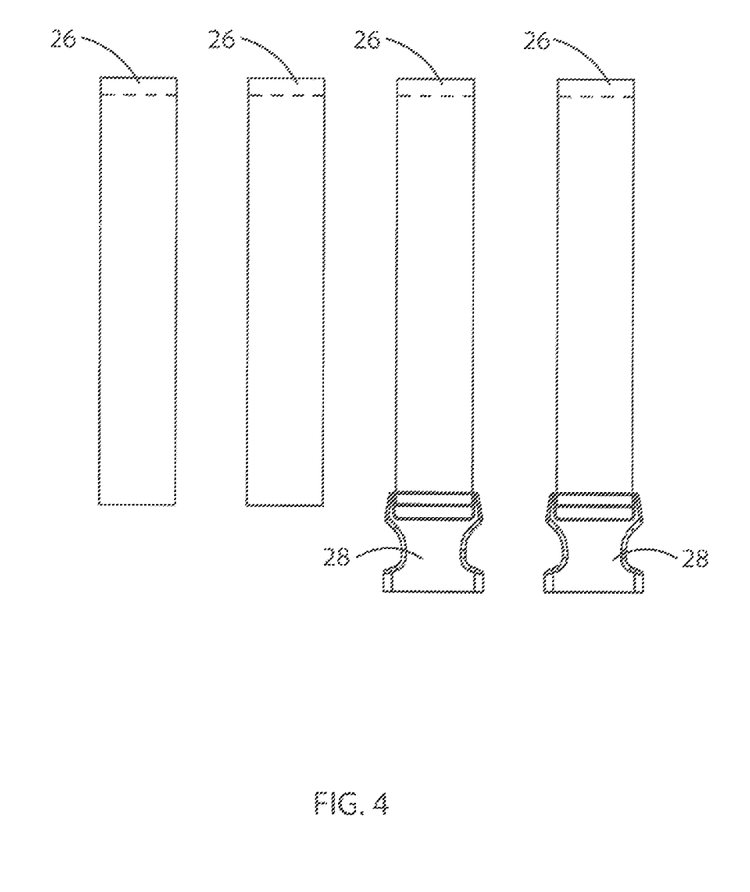
FIG. 4 illustrate four strap view with fasteners.

FIG. 3 item (24) shows a diaphragm pillow construction of Poly Fiber Cotton or made of foam padding encased in soft fleece and various fabrics. The pillow comprises of wherein the pillow are portable equipped for carrying and wearable on a driver's arms. FIG. 4 item (26) straps are placed in a midsection between the pillow and pouch. A driver portable wearable pillow comprises of straps or Velcro straps alongside configured for carrying and placement. The straps are attached to a said pillow used for a carry-on aide. The wearable pillow comprising of straps at top and bottom midsection along the side overlaps and used to carry the pillow and tie down for placement. The connectors item (28) snap and lock in the straps.

Figure 5:
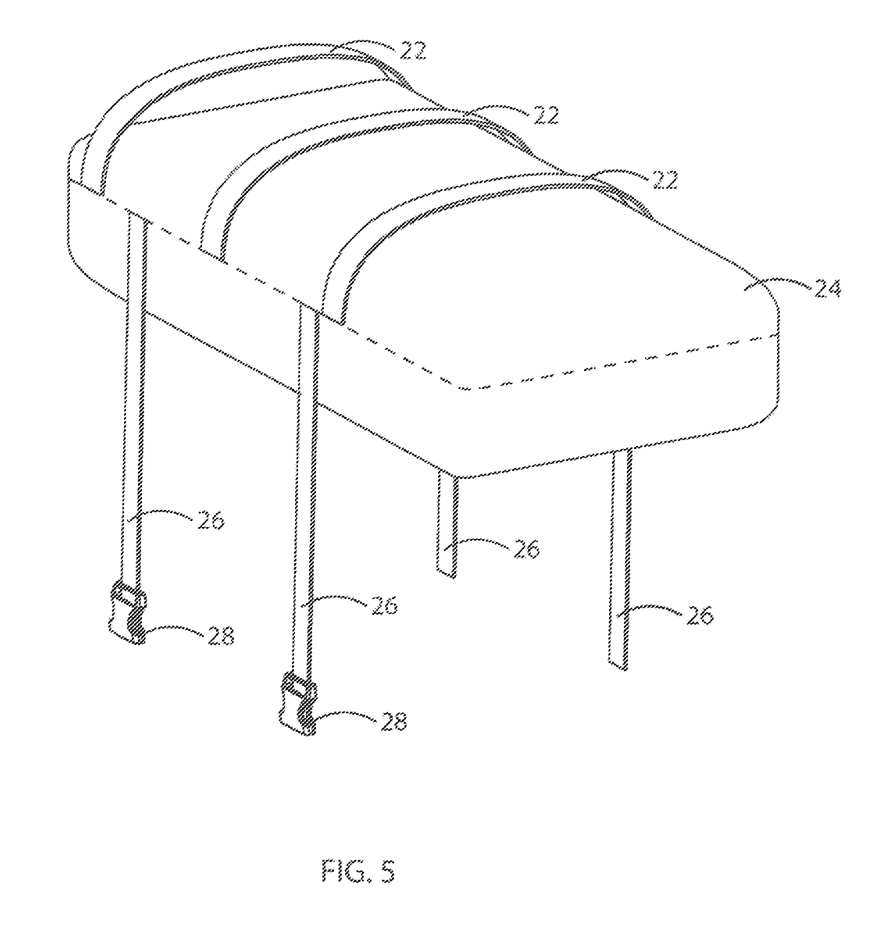
FIG. 5 depicts illustrates a perspective of driver's pillow.
Figure 6:
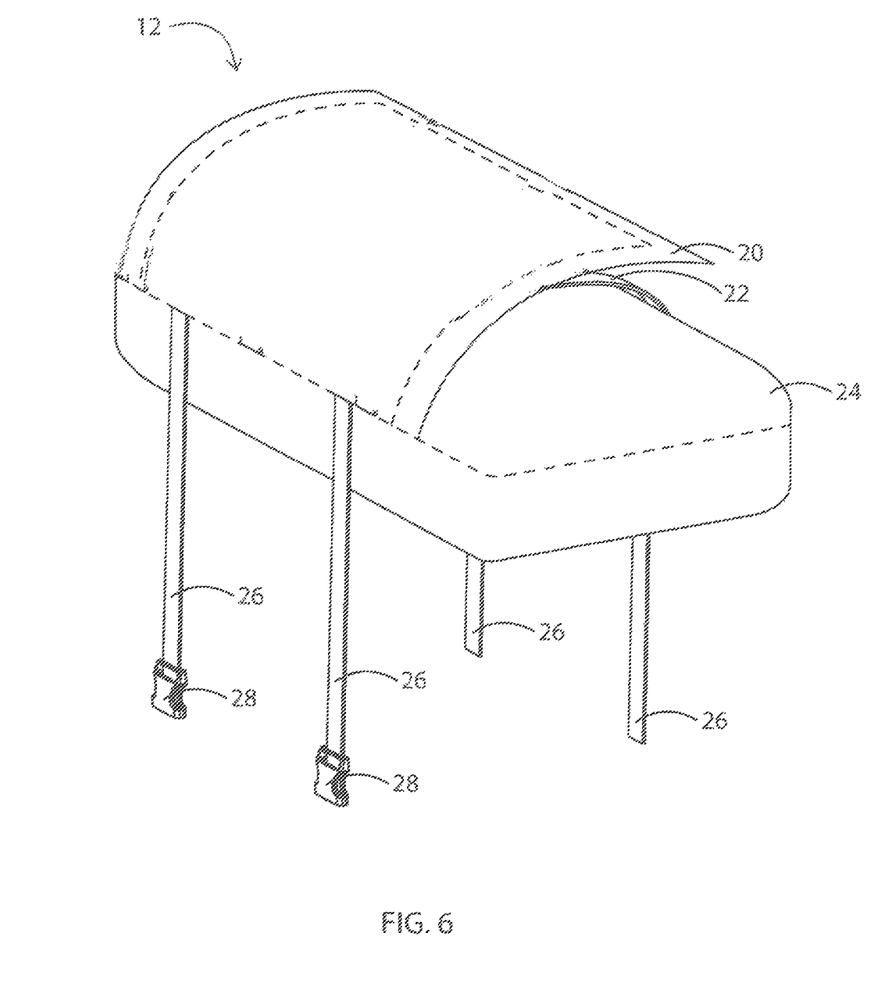
FIG. 6 perspective view of pouch cover.

FIG. 5 items (22), (24), (26), (28), and shows pouch opening (12), the elastic bands are under the pouch horizontal across the pillow gripping the drivers arms for snug fit on pillow (24) oval shape pillow length size small, medium and large according to length of drivers or passengers' arm to hand the straps (26) and (28) shown for carry on and tied in placement. FIG. 6 item (12) is top opening portable wearable pillow top opening Pouch layer (20) for snuggle fit for forearm to wrist it is placed over a said pillow attached allows comfort and support of elbows and shoulders to rest upon. Item (20) bottom opening pouch frame overlap the elastic bands (22) attached to said pillow midsection. Item (26) strap and (28) strap connectors for carrying pillows item (24) shows portable wearable pillow made of Poly Fiber Cotton or Foam Pads with soft fleece fabric worn on the arms of a driver. The portable accessory comprises of warmth and support of an arm snug fitted by elastic band under sewn to a said pouch (20) with elastic band holding the arm in place over a said pillow.

Figure 7:
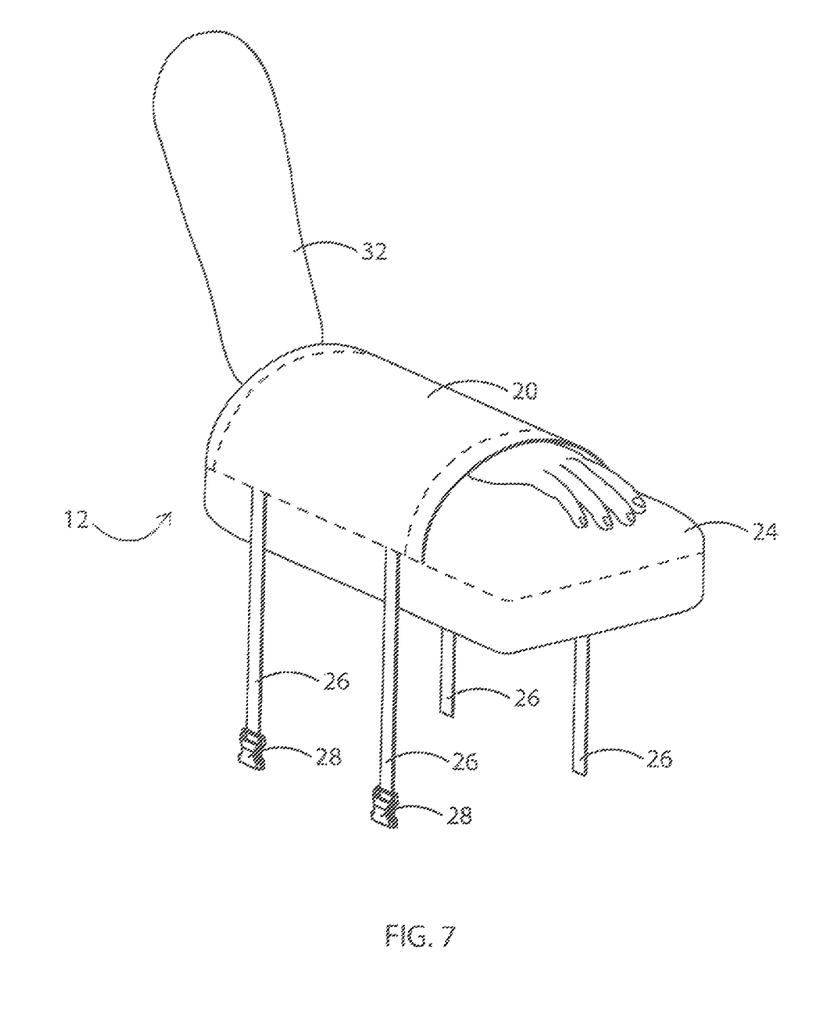
FIG. 7 perspective view of drivers.

FIG. 7 (12) Pouch top opening arm (32) enters the pouch (20) and elastic band grips and covers the top portion of arm snug fit by item (24) a pillow allowing the arm to rest on it items (26) carrying straps. While driving arms are free only attached to drivers' arms. The arm has free movement while driving according to DOT compliance. The pillow or foam padding are only attached to the arms of a driver or passenger. If an accident occurs while driving the pillow or foam pads will give some protection for the drivers face and upper body. It will give some resistance against flying glass and other objects from hitting the drivers or passengers face and upper body during a collision. Accidents or Collision will happen a normal instinct is for the driver's arms to go up to protect their face and upper body and wearing the wearable portable pillows will slow down some of the impact from flying glass and debris. These pillows will lower the risk of severity to the face and upper body of a driver.

Figure 8:
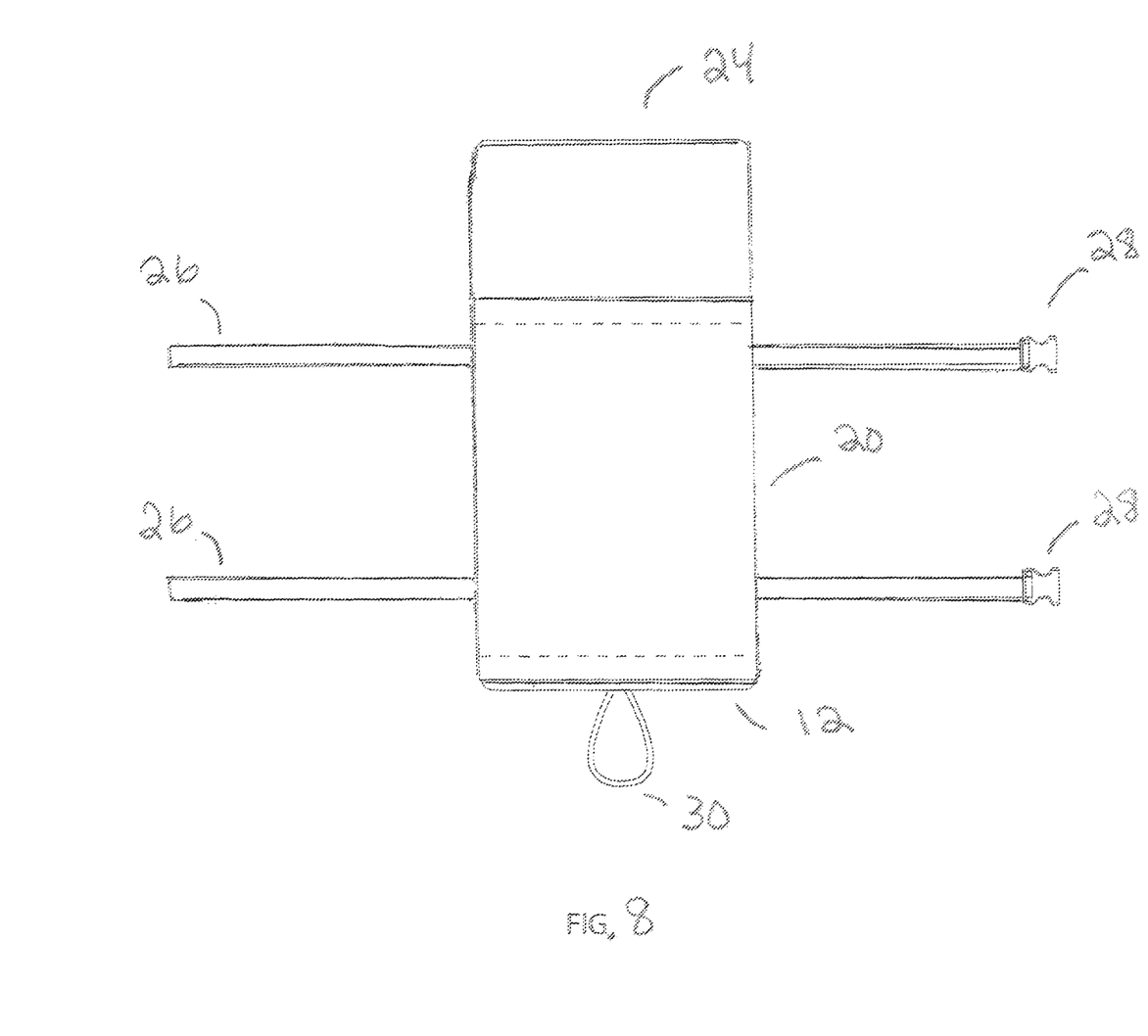
FIG. 8 front perspective view of driver's pillows.
Figure 9:
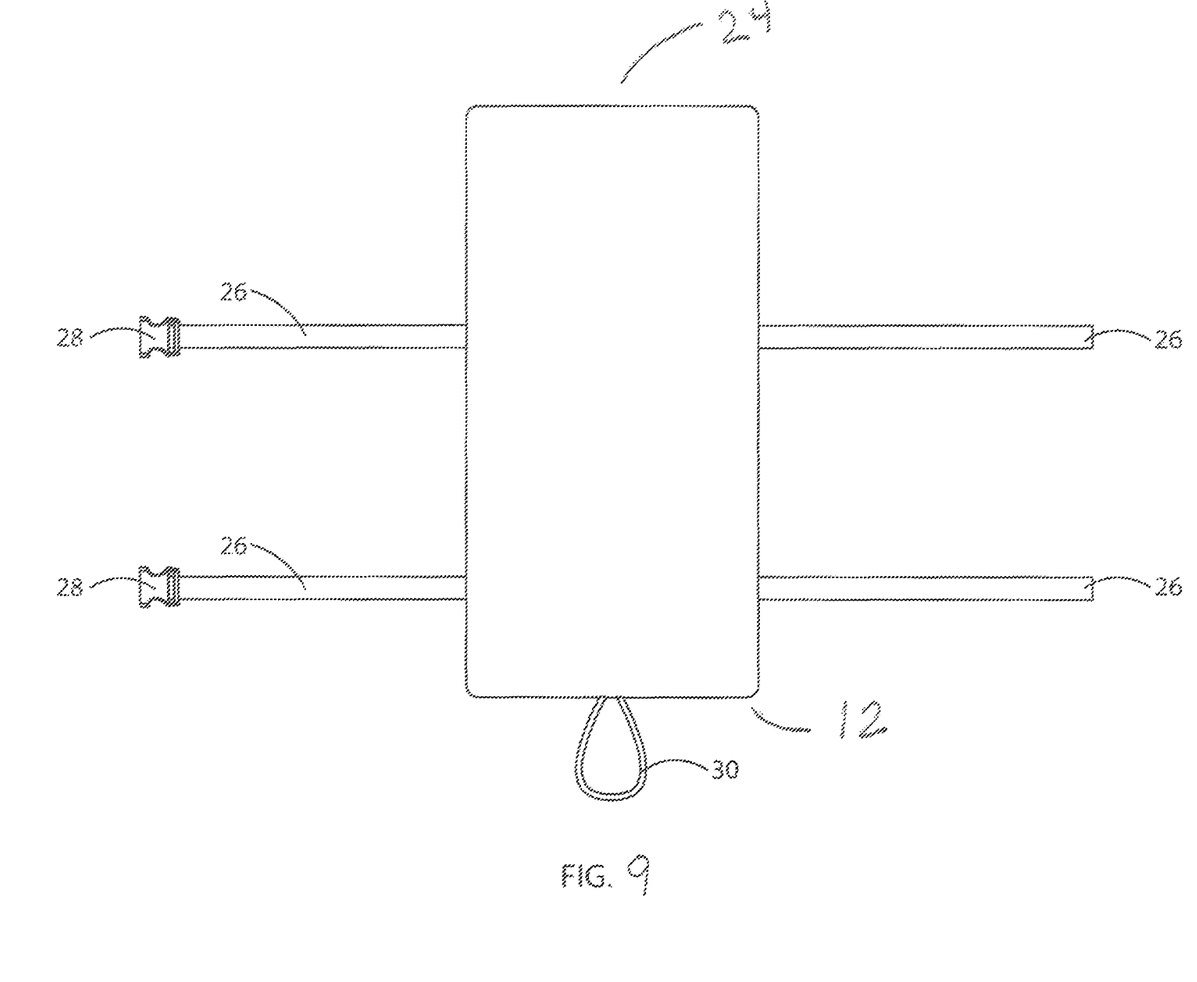
FIG. 9 back perspective view of pillow.
Figure 10:
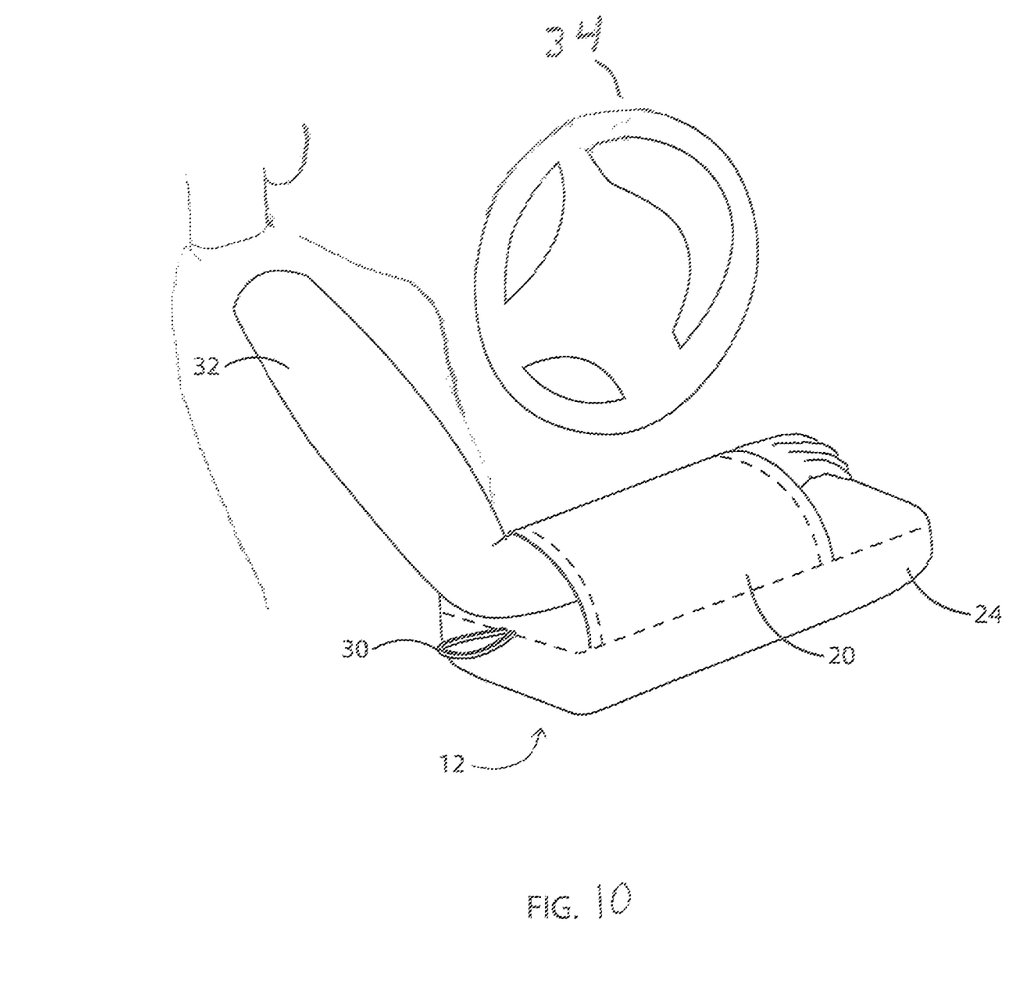
FIG. 10 show side view.

FIG. 8 shows frontal perspective view of a driver's pillow items (20), (12), (22), (26). (28), (30). FIG. 9 item (24) Back view (30) Hook loop is for hanging an object (24), (26) and (28). FIG. 10 Pouch opening (12), pouch cover layer (20) attached to the side section of a pillow (24) and (30) is hook loop and (32) drivers arm snug fitted into a drivers pillow and (34) is a driver's steering wheel. The portable accessory pillow embodiment poly fiber and foam padding will give some support and protection during a vehicle accidents collision, flying glass and debris hitting facial and upper body.

Figure 11:
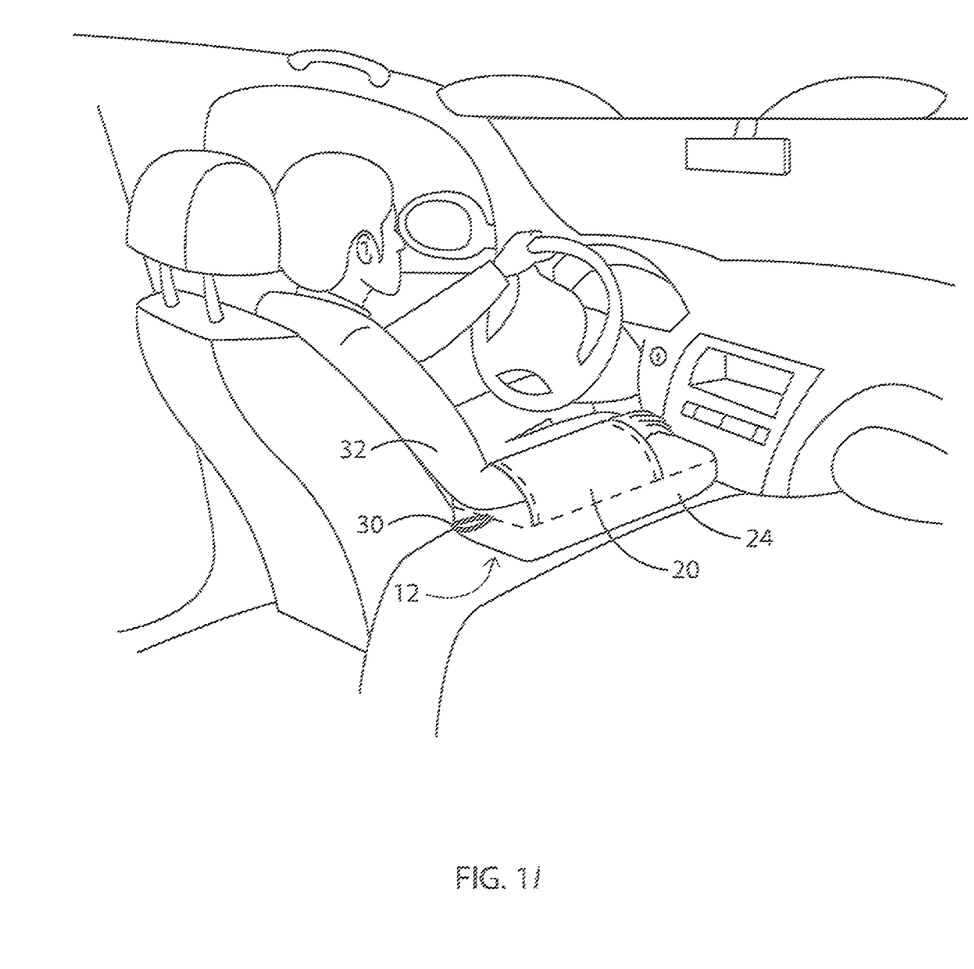
FIG. 11 is a schematic perspective view.

The arms of the driver and overlapped with a pouch opening for an arm placement and said pillow may lay across the driver's body and used for sports activities as an extra caution. The wearable portable pillows are worn on the arms and can be used as a protective device barrier during an auto accident collision by covering one's face with the arms against glass and flying debris while the pillows are attached. FIG. 11 Perspective view of a driver wearing a portable arm pillow.

We claim:

1. A portable trucker pillow comprising:
a substantially planar pillow member configured to support an arm of a wearer from a hand of the wearer to an elbow of the wearer, wherein the substantially planar pillow includes poly fiber cotton or foam pads with a soft, fleece, and stretchable outer fabric layer,
a plurality of elastic bands each having a first end attached to a first edge of the planar pillow member, and a second end attached to a second edge of the planar pillow member opposite to the first edge of the planar pillow member, wherein said plurality of elastic bands are configured to hold the arm of the wearer against the planar pillow member;
a sheath disposed over the plurality of elastic bands, wherein said sheath includes a first side attached at the first edge of the planar pillow member and a second side attached at the second side of the planar pillow member,
wherein said sheath is configured to receive the arm of the wearer and hug the arm against the planar pillow member, thereby providing support to the arm and shoulder of the wearer, and wherein said sheath covers the arm of the wearer from the wearer's elbow to a wrist of the wearer leaving the hand of the wearer free and substantially uncovered;
first and second strap portions attached to said first edge the planar pillow member,
third and fourth strap portions attached to said second edge of the planar pillow member,
wherein the first and second strap portions include respective, first and second strap connectors for respectively connecting to the third and fourth straps, thereby creating a set of carrying or tiedown straps for the portable trucker pillow; and
a hook loop located at a back end of the planar pillow member configured to hang the portable trucker pillow,
wherein the portable trucker pillow is configured to act as a barrier shield against flying glass and/or debris by protecting an upper face or body of a wearer or other person in a vehicle accident or collision or when the wearer is playing sports.

* * * * *